United States Patent [19]

Ngo

[11] Patent Number: 4,801,687

[45] Date of Patent: Jan. 31, 1989

[54] MONOCLONAL ANTIBODY PURIFICATION PROCESS USING PROTEIN A

[75] Inventor: That T. Ngo, Irvine, Calif.

[73] Assignee: Bioprobe International, Inc., Tustin, Calif.

[21] Appl. No.: 139,504

[22] Filed: Dec. 30, 1987

Related U.S. Application Data

[63] Continuation-in-part of Ser. No. 923,053, Oct. 27, 1986, abandoned.

[51] Int. Cl.$^4$ ............................................ A61K 39/395
[52] U.S. Cl. .................................... 530/387; 424/101;
424/85.8; 514/8; 514/21; 530/809; 530/830
[58] Field of Search ....................... 530/387, 809, 830;
424/101, 85; 514/8, 21

[56] References Cited

U.S. PATENT DOCUMENTS 3,850,798 11/1974 Sjoquist ........................... 520/387 X
4,582,875 4/1986 Ngo ................................... 525/54.1

FOREIGN PATENT DOCUMENTS 2755559 6/1978 Fed. Rep. of Germany ...... 520/387

OTHER PUBLICATIONS

Febs Letters, vol.-28 (1972), 73-76, Hztelm et al.
Immunochemistry, 15 (1978), 429-436, Ey et al.
Journal of Immunological Methods 62, (1983), 1-13, Lindmark et al.
Bulletin 1172, Bio-Rad Laboratories, Bio-Rad Chemical Division, Richmond,. Calif., (1984).

Primary Examiner—Howard E. Schain
Attorney, Agent, or Firm—Nilsson, Robbins, Dalgarn, Berliner, Carson & Wurst

[57] ABSTRACT

Immunoglobins are purified by adsorption upon an immobilized protein A adsorbent using a buffer having a pH of 7.5 to 10 and containing a combination of monovalent cations and polybasic anions in a concentration of about 0.6M to 1.75M.

20 Claims, No Drawings

MONOCLONAL ANTIBODY PURIFICATION PROCESS USING PROTEIN A

CROSS-REFERENCE TO RELATED APPLICATIONS

This application is a continuation-in-part of application Ser. No. 923,053, filed Oct. 27, 1986, entitled MONOCLONAL ANTIBODY PURIFICATION PROCESS, now abandoned.

BACKGROUND OF THE INVENTION

This invention relates to a process for purifying monoclonal antibodies. In one of its more particular aspects this invention relates to the purification of mammalian derived immunoglobulins.

With the discovery of techniques for the preparation of monoclonal antibodies derived from mammals, particularly mouse monoclonal antibodies, the need has arisen for purification of such monoclonal antibodies. Conventional purification techniques in which mixtures containing either polyclonal or monoclonal antibodies are passed through a suitable column to selectively adsorb the antibody from the mixture and the adsorbed antibody is later eluted from the column in purified form have been used for this purpose. However, the yield and purity of the isolated antibodies which can be obtained is limited by the lack of specificity of the column.

Previous processes for the purification of immunoglobulins, for example, suffered from the relatively low specificity of the adsorbent for the immunoglobulin. In one such process, various fractions of immunoglobulins from sera of different mammalian species were adsorbed upon protein A-Sepharose ® adsorbents at pH 7 or higher and eluted at pH's ranging from pH 2.5 to pH 6.5. [R. Lindmark, K. Thoren-Tolling and J. Sjoquist, "Binding of Immunoglobulins to Protein A and Immunoglobulin Levels in Mammalian Sera," *Journal of Immunological Methods,* 62:1 (1983)]. It was also known that binding of mouse IgG to protein A-Sepharose ® is pH sensitive and that optimum adsorption occurs using 0.1M sodium phosphate, pH 8.0 buffer. [P. L. Ey, S. J. Prowse and C. R. Jenkin, "Isolation of Pure IgG$_1$, IgG$_{2a}$ and IgG$_{2b}$ Immunoglobulins From Mouse Serum Using Protein A-Sepharose," *Immunochemistry,* 15:429 (1978)].

Recently, efforts have been made to increase the recovery of various immunoglobulins using specially formulated buffers. ["Mouse Monoclonal IgG$_1$, Purification with Affi-Gel ® Protein A," *Bulletin* 1172, Bio-Rad Laboratories, Bio-Rad Chemical Division, Richmond, Calif. (1984)].

It would be desirable to provide a purification process which would result in still higher yields of immunoglobulins.

Accordingly, it is an object of the present invention to provide an improved process for the purification of monoclonal antibodies and particularly immunoglobulins obtained from mammals.

It is another object of the present invention to provide such a process which does not require additional purification steps.

Anbther object of the present invention is to provide a rapid, convenient and economically practical process for improving the yield of monoclonal or polyclonal antibody realized in the adsorption thereof.

Other objects and advantages of this invention will become apparent from the following detailed disclosure.

SUMMARY OF THE INVENTION

The present invention provides a process for the purification of monoclonal and polyclonal antibodies, such as immunoglobulins, which is characterized by higher yields than have previously been realizable. The process includes the steps of mixing a medium containing immunoglobulins with a buffer solution having a pH in the range of about pH 7.5 to pH 10 which contains a hydrophobic interaction-promoting salt in the form of a combination of monovalent cations and polybasic anions in a concentration of about 0.6M to 1.75M to provide a buffered immunoglobulin medium, contacting the resulting buffered immunoglobulin medium with an immobilized protein A adsorbent to adsorb the immunoglobulins present in the buffered immunoglobulin medium upon the immobilized protein A adsorbent, washing the immobilized protein A adsorbent having immunoglobulins adsorbed thereon with the buffer solution, contacting the immobilized protein A adsorbent having immunoglobulins adsorbed thereon with a buffer solution having a pH in the range of about pH 3 to pH 6 to remove the adsorbed immunoglobulins from the immobilized protein A adsorbent, and recovering the removed immunoglobulins in substantially pure form. The yield of immunoglobulins realized according to the process of the present invehtion is increased by about twenty percent (20%) to more than ninety percent (90%) over yields previously obtainable.

DESCRIPTION OF THE PREFERRED EMBODIMENTS

The process of the present invention is useful in purifying immunoglobulins of various types including both monoclonal and polyclonal antibodies. It is applicable to many IgG subclasses such as IgG$_1$, IgG$_{2a}$, IgG$_{2b}$ and others. Antibodies from a wide variety of hosts including mouse, gerbil, rabbit, goat, horse, cow, and human antibodies can be purified using the process of the present invention. In general, it is applicable to any immunoglobulin for which protein A has a reasonable affinity. Immunoglobulins can be obtained from normal or immune mammalian serum, mammalian plasma, ascites fluid, hybridomas, tissue culture fluid, or any other source of antibodies.

The process of the present invention utilizes as an adsorbent an immobilized protein A. Although it is known that protein A interacts with various immunoglobulins, principally IgG from mammalian species, in the purified soluble state or as formalin-fixed S. aureus bacteria containing protein A, the use of protein A in other than an insolubilized state is not as practical as the utilization of, for example, protein A immobilized upon a cross-linked agarose. Protein A in its insolubilized form can conveniently be used in a column, which facilitates conducting the purification process.

Many suitable immobilized protein A adsorbents are commercially available. A purified protein A coupled to cross-linked agarose beads by chemically stable amide bonds can be obtained from Bio-Rad Laboratories, Richmond, Calif. as Affi-Gel ® Protein A. Protein A-Agarose is also available from Zymed Laboratories, Burlingame, Calif. This product is described as a pure protein A coupled to CNBr-activated Sepharose ® 4B. A similar product, Protein A Sepharose ® CL-4B is also available from Pharmacia Fine Chemicals, Uppsala, Sweden. Protein A-Ultrogel® is available from Reactifs IBF, France. It is described as a biospecific affinity chromatography sorbent able to interact with different immunoglobulins G from different mammals and is prepared by immobilizing electrophoretically pure protein A to a glutaraldehyde-activated gel. Protein A covalently coupled to cross-linked beaded agarose is also available from Pierce Chemical Co.

An immobilized protein A can also be provided using the techniques disclosed in U.S. Pat. No. 4,582,875, assigned to the same assignee as the present invention, the disclosure of which is hereby incorporated by reference. This patent generally teaches the activation of hydroxyl group-containing polymeric carriers using 2-fluoro-1-methylpyridinium toluene-4-sulfonate (FMP). Such activated polymers are commercially available from BioProbe International, Inc., Tustin, Calif. Avid-Gel ™ FMP-activated hydrophilic gel is an FMP-activated polymer of N-acryloyl-2-amino-2-hydroxymethyl-1,3-propanediol (Trisacryl GF 2000, Reactifs IBF, France). Avid-Gel F ™ FMP-activated hydrophilic gel is an FMP-activated hydrophilic vinyl alcohol polymer composed exclusively of C, H and O atoms (Fractogel TSK, E. Merck, Darmstadt, Germany). Both can be used to provide an immobilized protein A.

The first step in the process of the present invention requires a buffer having a pH in the range of about pH 7.5 to pH 10 and a combination of monovalent cations and polybasic anions in a concentration of about 0.6M to 1.75M. Any buffer may be used to provide the desired pH. For example glycine buffer, borate buffer or tris buffer can be used. The concentration of buffer should be in the range of about 0.01M to 0.25M.

Where the monovalent cations are potassium ions and the polybasic anions are phosphate ions the potassium ions and phosphate ions can be provided by the use of potassium phosphate either in the form of tripotassium phosphate, $K_3PO_4$, dipotassium hydrogen phosphate, $K_2HPO_4$ or monopotassium dihydrogen phosphate, $KH_2PO_4$, since the pH of the medium controls the proportion of the various phosphate ions which are present. The potassium ions and phosphate ions should be present in a concentration in the range of about 0.6M to 1.75M. A concentration of about 1.0M to 1.5M has been found especially satisfactory.

Other combinations of monovalent cations and polybasic anions which have adequate solubilities at the high concentrations used in the present invention, include ammonium phosphates in concentrations of about 1.0M to 1.5M, ammonium sulfates in concentrations of about 1.0M to 1.5M and sodium sulfates in concentrations of about 1.0M to 1.25M. Other combinations may be used as well so long as the salts do not precipitate at the concentrations used.

As pointed out above, the adsorbent is preferably used in a column to facilitate contact with the immunoglbulins to be purified. Prior to application of the medium containing the impure immunoglobulins to the column, the column is equilibrated with several bed volumes of buffer containing the combination of to the column, the column is equilibrated with several bed volumes of buffer containing the combination of monovalent cations and polybasic anions at concentrations in the range of about 0.6M to 1.75M. This ensures that the environment is optimum for binding the immunoglobulins to the column. The medium containing the immunoglobulins to be purified, such as an immune serum or other source of immunoglobulins is mixed with the buffer containing the combination of monovalent cations and polybasic anions. The resulting mixture is then applied to the column, resulting in adsorption of the immunoglobulins to the column. The column is then washed with additional buffer containing the combination of monovalent cations and polybasic anions in order to elute from the column impurities which are not strongly adsorbed to the column. The immunoglobulins on the other hand are strongly adsorbed to the column because of the enhanced affinity of the adsorbent for the immunoglobulins as a result of the presence of the buffer containing the combination of monovalent cations and polybasic anions. Following removal of the undesired impurities by washing with the same buffer solution, the purified immunoglobulins are eluted from the column by means of a buffer having an acidic pH, namely a pH in the range of about pH 3.0 to pH 6.0. At pH 6.0 a part of the immunoglobulins, principally the $IgG_1$ fraction, is eluted. As the pH is lowered the remainder of the immunoglobulins, including the $IgG_{2a}$ and $IgG_{2b}$ fractions, is eluted. The immunoglobulins can be eluted using a pH 3.0 buffer, which is effective to elute all of the immunoglobulins. However, if desired, a fraction of the immunoglobulins can be eluted at pH 6.0. Various other fractions can be eluted, if so desired, by lowering the pH between pH 6.0 and pH 3.0. By lowering the pH in steps, it is possible to isolate purified fractions of immunoglobulins which contain specific immunoglobulins as desired. Any buffer can be used for elution. For example an acetic acid-acetate buffer can be used for this purpose. A buffer concentration in the range of about 0.01M to 0.25M can be used. A buffer concentration of about 0.05M to 0.10M is especially preferred.

The isolated immunoglobulins or fractions thereof can be recovered in yields which are as much as ninety percent (90%) higher than yields previously obtainable. Even yields obtained using the most sophisticated techniques previously available can be improved by as much as twenty to thirty percent (20-30%).

The invention will be better understood by reference to the following examples which are intended for purposes of illustration and are not to be construed as in any way limiting the scope of the present invention which is defined in the claims appended hereto.

EXAMPLE 1

To a 3 ml column was added 1 ml of immobilized protein A (Protein A Avid Gel ™, BioProbe International, Inc. Tustin, Calif.). The column was equilibrated with 10 ml of a 0.025M glycine buffer containing 1.2M $K_2HPO_4$. The pH was varied from pH 8.0 to pH 10.0. A quantity of 1 ml of normal mouse serum (from Granite Diagnostics, Burlington, N.C.) was diluted with 1 ml of buffer and applied to the column. Then the column was washed with 5-10 ml of buffer. The immunoglobulins which were adsorbed on the column were eluted with 5 ml of 0.1M acetic acid, sodium acetate buffer, pH 3.5. The yields of immunoglobulins obtained ranged from eighty percent (80%) to one hundred percent (100%) in the pH range of pH 8.0 to pH 10.0, the yields increasing with pH. By comparison, use of a phosphate buffered saline (PBS), pH 9.0 resulted in a yield of only twenty percent (20%).

EXAMPLE 2

To a 3 ml column was added 1 ml of immobilized protein A (Affi-Gel® Protein A, Bio-Rad Laboratories, Richmond, Calif.). The column was equilibrated with 10 ml of a 0.025M glycine, pH 9.1 buffer containing 1.2M $K_2HPO_4$. A quantity of 1 ml of normal mouse serum (from Pel-Freez Biological, Rogers, Ark.) was diluted with 1 ml of buffer and applied to the column. Then the column was washed with 5-10 ml of buffer. The immunoglobulins contained in the serum sample were eluted from the column with 5 ml of 0.1M acetic acid sodium acetate buffer, pH 3.5 in a yield of 13.8 mg. This yield was twenty percent (20%) higher than was obtained using a commercially available buffer solution (Affi-Gel® Protein A MAPS Buffer, Bio-Rad Laboratories, Richmond, Calif.).

EXAMPLE 3

To a 3 ml column was added 1 ml of immobilized Protein A (Protein A Avid Gel ™, BioProbe International, Inc., Tustin, Calif.). The column was equilibrated with 10 ml of a 0.025M glycine, 0.025M sodium borate buffer, pH 9.1, containing varying concentrations of $K_2HPO_4$ as shown in Table 1. A quantity of 1 ml of normal mouse serum (obtained from Pel-Freez Biological, Rogers, Ark.) was diluted with 1 ml of buffer and applied to the column. Then the column was washed with 5-10 ml of buffer. The immunoglobulins adsorbed on the column were eluted with 5 ml of 0.1M acetic acid-sodium acetate buffer, pH 3.5. The yields of immunoglobulins obtained are shown in Table 1.

TABLE I

| $K_2HPO_4$ CONCENTRATION (M) | YIELD OF IMMUNOGLOBULINS (mg.) |
|---|---|
| 0.6 | 11.0 |
| 0.8 | 13.1 |
| 1.0 | 13.5 |
| 1.2 | 14.5 |

Much higher concentration of $K_2HPO_4$ resulted in precipitation of the immunoglobulins.

EXAMPLE 4

To a 3 ml column was added 1 ml of immobilized protein A (Protein A Avid Gel ™, Bioprobe International, Inc., Tustin, Calif.). The column was equilibrated with 10 ml of 0.1M glycine, 0.1M sodium borate, 0.1M sodium phosphate buffer, pH 9.1, containing varying concentrations of $K_2HPO_4$ as shown in Table 2. A quantity of 1 ml of mouse monoclonal antibody to rat Kappa chain from ascites fluid was diluted with 1 ml of the buffer and applied to the column. The ascites fluid was obtained as follows. BALB/c mice were immunized by injection of purified rat Kappa chain emulsified with complete Freund's adjuvant. Spleens from immunized mice were removed aseptically and minced with tweezers. Mouse myeloma RG 11-15 cells were fused with spleen cells from immunized mice by using fifty percent (50%) poly(ethylene glycol). After the selection in HAT medium and screening for the hybridoma clones that secrete antibody, the hybridoma cells were injected intraperitoneally into BALB/c mice that have been irradiated with 500 rad gamma-ray. Ascites fluid harvested was clarified by low-speed centrifugation and purified by using immobilized protein A. Following application of the monoclonal antibody the column was washed with 5-10 ml of the same buffer. The immunoglobulins which were adsorbed on the immobilized Protein A were eluted with 5 ml of 0.1M acetic acid sodium acetate buffer, pH 3.5. The yield of immunoglobulins obtained are shown in Table 2. For comparison, the immunoglobulin yields obtained by using MAPS buffer and phosphate buffered saline with 2M NaCl are also shown in Table 2.

TABLE 2

| POTASSIUM PHOSPHATE (M) | YIELD OF IMMUNOGLOBULINS (mg.) |
|---|---|
| 0.5 | 1.3 |
| 0.75 | 2.4 |
| 1.0 | 3.3 |
| 1.25 | 4.8 |
| 1.50 | 5.3 |
| 1.75 | 6.0 |
| MAPS Buffer | 3.1 |
| Phosphate Buffered Saline with 2M NaCl | 1.2 |

EXAMPLE 5

To a 3 ml column was added 1 ml of immobilized protein A (Protein A Avid-Gel ™, BioProbe International, Inc., Tustin, Calif.). The column was equilibrated with 10 ml of a 0.05M Tris (hydroxymethyl) aminomethane (Tris) buffer, pH 8.5, containing 1.0M $K_2HPO_4$. A quantity of 1 ml of mouse monoclonal antibody from ascites fluid was diluted with 1 ml of buffer and applied to the column. Then the column was washed with 5-10 ml of buffer. The immunoglobulins which were adsorbed on the column were eluted with 5 ml of 0.1M acetic acid-sodium acetate buffer, pH 3.5. The yield of immunoglobulins obtained was 2.9 mg.

EXAMPLE 6

The procedure of Example 5 was followed except that the buffer used was a 0.25M glycine, 0.1M Tris buffer, pH 8.9, containing 1.5M $K_2HPO_4$. The yield of immunoglobulins obtained was 4.49 mg.

EXAMPLE 7

To a 3 ml. column was added 1 ml. of immobilized protein A (Protein A Avid-Gel ™, BioProbe International, Inc., Tustin, Calif.). The column was equilibrated with 10 ml. of a 0.1M Tris (hydroxymethyl) aminomethane buffer, the pH varying as shown in Table 3, which contained varying concentrations of hydrophobic interaction-promoting salts, as shown in Table 3. A quantity of 3 ml. human immunoglobulin solution and 6 ml. of the above buffer mixture were well mixed and applied to the column. Then the column was washed with 10 ml. buffer. The bound immunoglobulins were eluted from the column with 10 ml. of 0.1M acetic acid-sodium acetate buffer, pH 3.5. The quantity of immunoglobulins in the elute was determined by measuring the absorbance of the eluate solution at 280 nm. The results are shown in Table 3.

TABLE 3

| Salt | pH | Concentration M | Quantity of Immunoglobulins in Eluate, mg. |
|---|---|---|---|
| Ammonium Phosphate | 7.5 | 0.0 | 22.1 |
| Ammonium Phosphate | " | 0.5 | 18.8 |

TABLE 3-continued

| Salt | pH | Concentration M | Quantity of Immunoglobulins in Eluate, mg. |
|---|---|---|---|
| Ammonium Phosphate | " | 1.0 | 23.6 |
| Ammonium Phosphate | " | 1.5 | 28.4 |
| Ammonium Sulfate | " | 0.0 | 22.1 |
| Ammonium Sulfate | " | 0.5 | 20.5 |
| Ammonium Sulfate | " | 1.0 | 23.0 |
| Ammonium Sulfate | " | 1.5 | 35.2 |
| Sodium Sulfate | " | 0.0 | 22.1 |
| Sodium Sulfate | " | 0.5 | 21.7 |
| Sodium Sulfate | " | 1.0 | 34.8 |
| Ammonium Phosphate | 8.5 | 0.0 | 19.1 |
| Ammonium Phosphate | " | 0.5 | 13.1 |
| Ammonium Phosphate | " | 1.0 | 19.8 |
| Ammonium Phosphate | " | 1.5 | 27.3 |
| Sodium Sulfate | " | 0.0 | 19.1 |
| Sodium Sulfate | " | 0.5 | 16.7 |
| Sodium Sulfate | " | 1.0 | 24.0 |

The present invention provides an improved process for the purification of immunoglobulins which is rapid and convenient. Yields of immunoglobulins improved by twenty to over ninety percent (20-90%) over previous methods are realizable by practicing the process of the present invention.

The foregoing description of the invention has been directed to particular preferred embodiments for purposes of explanation and illustration. It will be apparent, however, to those skilled in the art, that many modifications and changes in the particular methods and materials may be made without departure from the scope and spirit of the invention. For example, the adsorption process can be carried out in a batchwise manner or in other buffered solutions. It is applicant's intention in the following claims to cover all such equivalents, modifications and changes that fall within the true spirit and scope of the invention.

What is claimed is:

1. A process for the purification of immunoglobulins which comprises:
   mixing a medium containing immunoglobulins with a buffer solution having a pH in the range of about pH 7.5 to pH 10 and containing a combination of monovalent cations and polybasic anions in a concentration of about 0.6M to 1.75M to provide a buffered immunoglobulin medium;
   contacting said buffered immunoglobulin medium with an immobilized protein A adsorbent to adsorb the immunoglobulins present in said buffered immunoglobulin medium upon said immobilized protein A adsorbent;
   washing the immobilized protein A adsorbent having immunoglobulins adsorbed thereon with said buffer solution;
   contacting said immobilized protein A adsorbent having immunoglobulins adsorbed thereon with a buffer solution having a pH in the range of about pH 3 to pH 6 to remove the adsorbed immunoglobulins from the immobilized protein A adsorbent; and
   recovering the removed immunoglobulins in substantially pure form.

2. A process according to claim 1 wherein the contacting of said buffered immunoglobulin medium with said immobilized protein A adsorbent is accomplished in a column of said immobilized protein A adsorbent.

3. A process according to claim 1 wherein said medium containing immunoglobulins is a normal mammalian serum.

4. A process according to claim 1 wherein said medium containing immunoglobulins is an immune mammalian serum.

5. A process according to claim 1 wherein said medium is a mammalian plasma.

6. A process according to claim 1 wherein said medium is mammalian ascites fluid.

7. A process according to claim 1 wherein said medium is obtained from a hybridoma.

8. A process according to claim 1 wherein said medium is a tissue culture fluid.

9. A process according to claim 1 wherein said buffer solution having a pH in the range of about pH 7.5 to pH 10 is a glycine buffer.

10. A process according to claim 1 wherein said buffer solution having a pH in the range of about pH 7.5 to pH 10 is a borate buffer.

11. A process according to claim 1 wherein said buffer solution having a pH in the range of about pH 7.5 to pH 10 is a tris (hydroxymethyl) aninomethane buffer.

12. A process according to claim 1 wherein said buffer solution having a pH in the range of about pH 7.5 to pH 10 has a concentration in the range of about 0.01M to 0.25M.

13. A process according to claim 1 wherein said immobilized protein A adsorbent is protein A chemically bonded to cross-linked agarose.

14. A process according to claim 1 wherein said immobilized protein A adsorbent is protein A chemically bonded to a 2-fluoro-1-methylpyridinium toluene-4-sulfonate activated hydroxyl group-containing polymeric carrier.

15. A process according to claim 1 wherein said buffer solution having a pH in the range of about pH 3 to pH 6 is an acetic acid-acetate buffer.

16. A process according to claim 1 wherein said buffer solution having a pH in the range of about pH 3 to pH 6 has a concentration in the range of about 0.01M to 0.25M.

17. A process according to claim 1 wherein said buffer solution contains potassium ions and phosphate ions in a concentration of about 1.0M to 1.5M.

18. A process according to claim 1 wherein said buffer solution contains ammonium ions and phosphate ions in a concentration of about 1.0M to 1.5M.

19. A process according to claim 1 wherein said buffer solution contains ammonium ions and sulfate ions in a concentration of about 1.0M to 1.5M.

20. A process according to claim 1 wherein said buffer solution contains sodium ions and sulfate ions in a concentration of about 1.0M to 1.25M.

* * * * *